(12) United States Patent
Hauser et al.

(10) Patent No.: US 11,723,673 B2
(45) Date of Patent: *Aug. 15, 2023

(54) METHOD AND APPARATUS TO SELECT VIBRATION

(71) Applicant: Medtronic Xomed, Inc., Jacksonville, FL (US)

(72) Inventors: Bret Hauser, Flower Mound, TX (US); Thaddeus S. Milburn, Pantego, TX (US)

(73) Assignee: Medtronic Xomed, Inc., Jacksonville, FL (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/208,389

(22) Filed: Mar. 22, 2021

(65) Prior Publication Data

US 2021/0228218 A1    Jul. 29, 2021

Related U.S. Application Data

(63) Continuation of application No. 16/276,090, filed on Feb. 14, 2019, now Pat. No. 10,952,748, which is a continuation of application No. 14/926,787, filed on Oct. 29, 2015, now Pat. No. 10,206,691.

(51) Int. Cl.
    *A61B 17/16*    (2006.01)
(52) U.S. Cl.
    CPC ...... *A61B 17/1622* (2013.01); *A61B 17/1615* (2013.01); *A61B 17/1628* (2013.01); *A61B 17/1633* (2013.01)

(58) Field of Classification Search
    CPC . A61B 17/16; A61B 17/1622; A61B 17/1624; A61B 17/1626; A61B 17/1628; A61B 17/1633; B23Q 11/0032
    See application file for complete search history.

(56) References Cited

U.S. PATENT DOCUMENTS

| | | | | |
|---|---|---|---|---|
| 5,222,956 A | * | 6/1993 | Waldron | A61B 17/162 279/75 |
| 5,601,560 A | * | 2/1997 | Del Rio | A61B 17/162 408/231 |
| 5,741,263 A | * | 4/1998 | Umber | A61C 1/18 279/75 |
| 5,833,246 A | * | 11/1998 | Trott | A61C 1/144 279/131 |

(Continued)

FOREIGN PATENT DOCUMENTS

| | | |
|---|---|---|
| CN | 1247782 A | 3/2000 |
| CN | 104146741 A | 11/2014 |

(Continued)

OTHER PUBLICATIONS

Japanese Office Action (With English Translation) regarding Japanese Application No. 2018-521879, dated May 14, 2021.

(Continued)

*Primary Examiner* — Eric S Gibson
(74) *Attorney, Agent, or Firm* — Carter, DeLuca & Farrell LLP

(57) ABSTRACT

Disclosed is an assembly for holding a tool. The assembly may selectively reduce and/or eliminate vibrations received and felt by a user. Reducing vibrations may reduce or eliminate chatter at a working end of a tool.

22 Claims, 5 Drawing Sheets

(56) References Cited

U.S. PATENT DOCUMENTS

| | | | | |
|---|---|---|---|---|
| 5,888,200 | A * | 3/1999 | Walen | B25F 3/00 606/167 |
| 6,135,461 | A * | 10/2000 | Below | B25D 17/088 279/38 |
| 6,780,189 | B2 * | 8/2004 | Tidwell | A61B 17/1633 606/80 |
| 7,879,037 | B2 * | 2/2011 | Brunnett | A61B 17/1631 606/79 |
| 8,273,097 | B2 * | 9/2012 | Malla | A61M 3/0229 606/167 |
| 10,206,691 | B2 * | 2/2019 | Hauser | A61B 17/32002 |
| 10,952,748 | B2 * | 3/2021 | Hauser | A61B 17/1633 |
| 2002/0058958 | A1 * | 5/2002 | Walen | A61B 17/32002 606/170 |
| 2002/0074046 | A1 | 6/2002 | Sudani et al. | |
| 2002/0151902 | A1 * | 10/2002 | Riedel | A61B 17/162 606/80 |
| 2002/0165549 | A1 * | 11/2002 | Owusu-Akyaw | A61B 17/1628 606/80 |
| 2003/0163134 | A1 * | 8/2003 | Riedel | B23B 31/1072 606/167 |
| 2005/0245318 | A1 | 11/2005 | Del Rio et al. | |
| 2006/0053974 | A1 * | 3/2006 | Blust | A61B 17/162 81/3.07 |
| 2006/0088182 | A1 | 4/2006 | Takayama et al. | |
| 2006/0241630 | A1 * | 10/2006 | Brunnett | A61B 17/1624 606/80 |
| 2007/0239187 | A1 * | 10/2007 | Brunnett | A61B 17/32 606/172 |
| 2008/0208195 | A1 * | 8/2008 | Shores | A61B 17/1633 29/525.01 |
| 2008/0208229 | A1 * | 8/2008 | Tidwell | A61B 17/1628 606/167 |
| 2008/0290613 | A1 | 11/2008 | Haimer | |
| 2010/0063524 | A1 * | 3/2010 | McCombs | A61B 17/1628 606/167 |
| 2012/0259337 | A1 * | 10/2012 | del Rio | A61B 17/162 29/428 |
| 2017/0120451 | A1 * | 5/2017 | Hauser | A61B 17/1628 |
| 2018/0055532 | A1 * | 3/2018 | Messerly | H01L 41/0536 |
| 2019/0175194 | A1 * | 6/2019 | Hauser | A61B 17/1622 |
| 2021/0228218 | A1 * | 7/2021 | Hauser | A61B 17/1615 |

FOREIGN PATENT DOCUMENTS

| | | |
|---|---|---|
| JP | H 02-34822 A | 2/1990 |
| JP | H03130071 A | 6/1991 |
| JP | 2000052114 A | 2/2000 |
| JP | 2002-357279 A | 12/2002 |
| JP | 2006-128938 A | 5/2006 |
| JP | 2010528775 A | 8/2010 |
| JP | 2012501741 A | 1/2012 |
| KR | 100888997 B1 | 3/2009 |
| WO | 2008154256 A2 | 12/2008 |
| WO | 2010028001 A2 | 3/2010 |

OTHER PUBLICATIONS

Examination Report dated Jan. 28, 2021 in corresponding Australian Application No. 2016346189.
Examination Report dated Jul. 30, 2020 in corresponding Australian Application No. 2016346189.
International Preliminary Report on Patentability dated May 11, 2018 in corresponding International Application No. PCT/US2016/058689.
International Search Report and Written Opinion dated Feb. 3, 2017 for PCT/US2016/058689 claiming benefit of U.S. Appl. No. 14/926,787, filed Oct. 29, 2015.
Office Action dated Dec. 2, 2020 in corresponding Japanese Application No. 2018-521879.
Office Action dated Jun. 1, 2020 in corresponding Chinese Application No. 201680070401.1.
Office Action dated Mar. 1, 2019 in corresponding/related European Application No. 16791240.1.
Office Action dated Nov. 2, 2020 in corresponding Japanese Application No. 2018-521879.
U.S. Appl. No. 14/926,787, U.S. Pat. No. 10,206,691, filed Oct. 29, 2015, Hauser, et al.
U.S. Appl. No. 16/276,090, U.S. Pat. No. 10,952,748, filed Feb. 14, 2019, Hauser, et al.

* cited by examiner

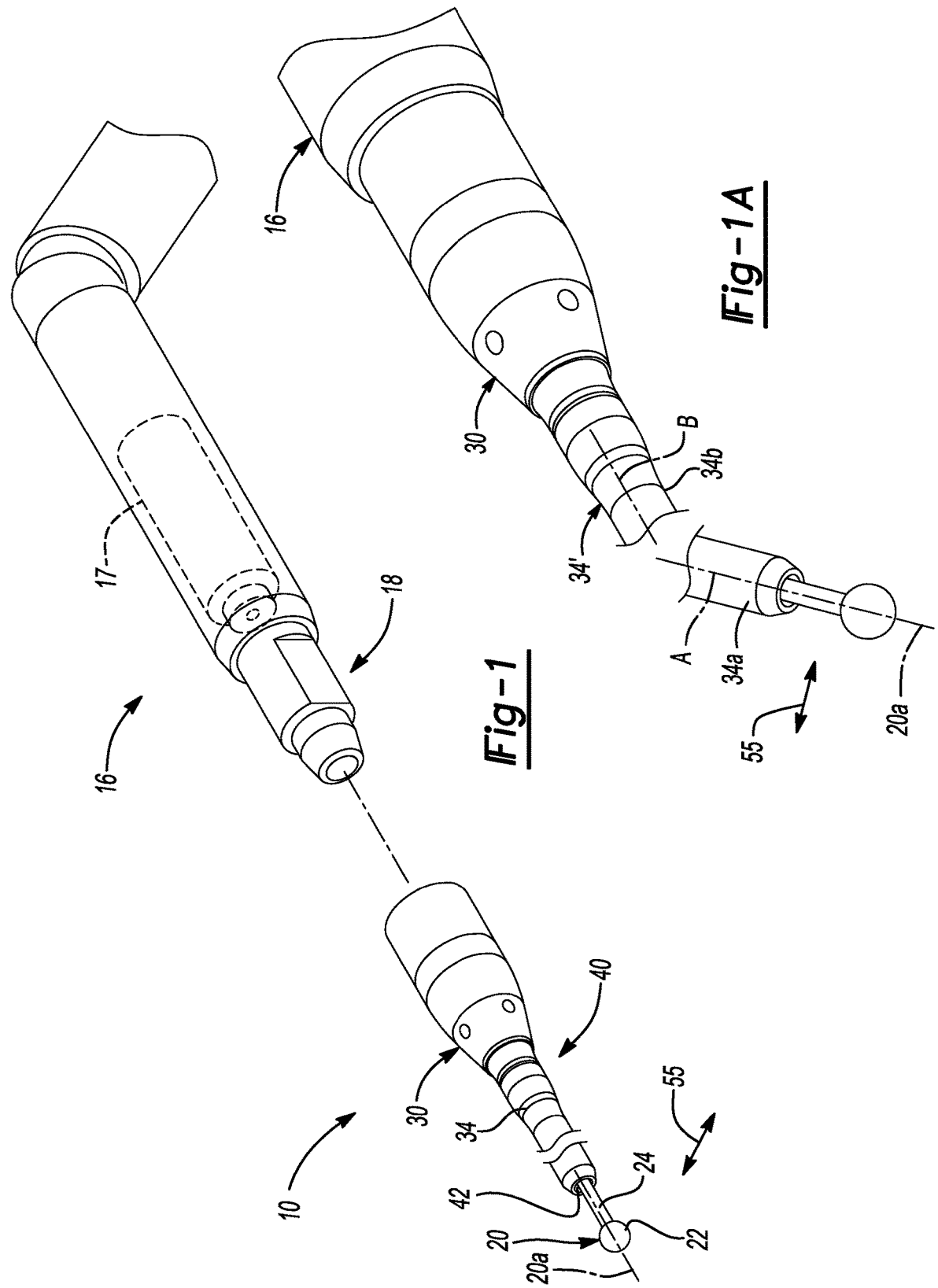

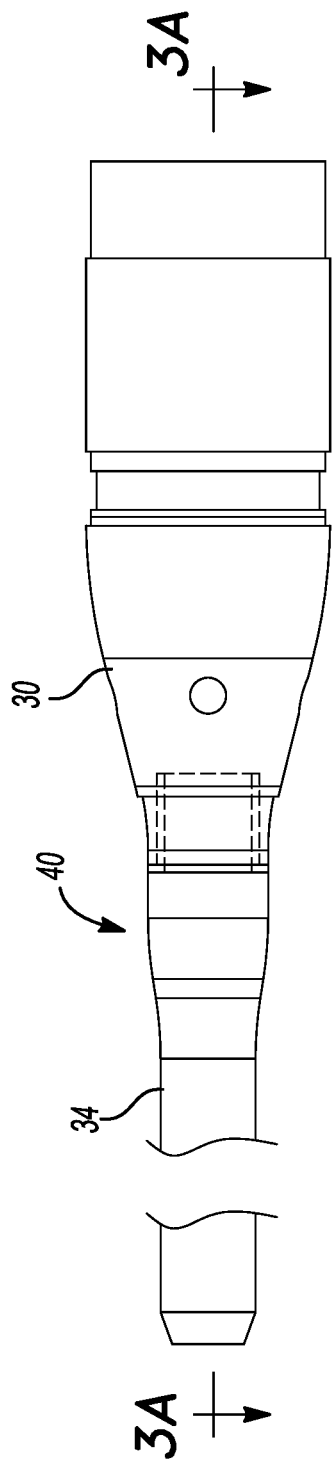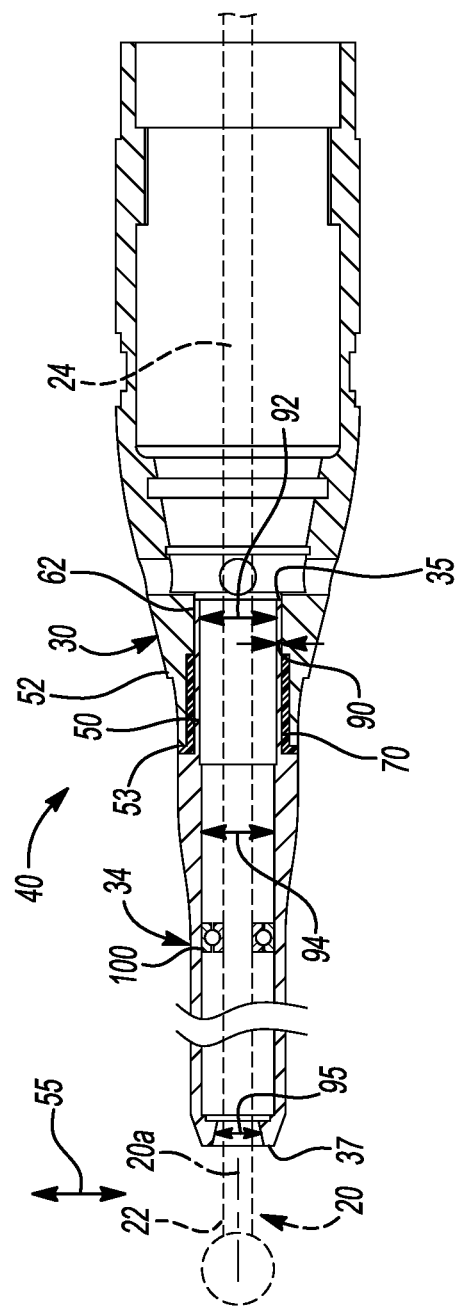

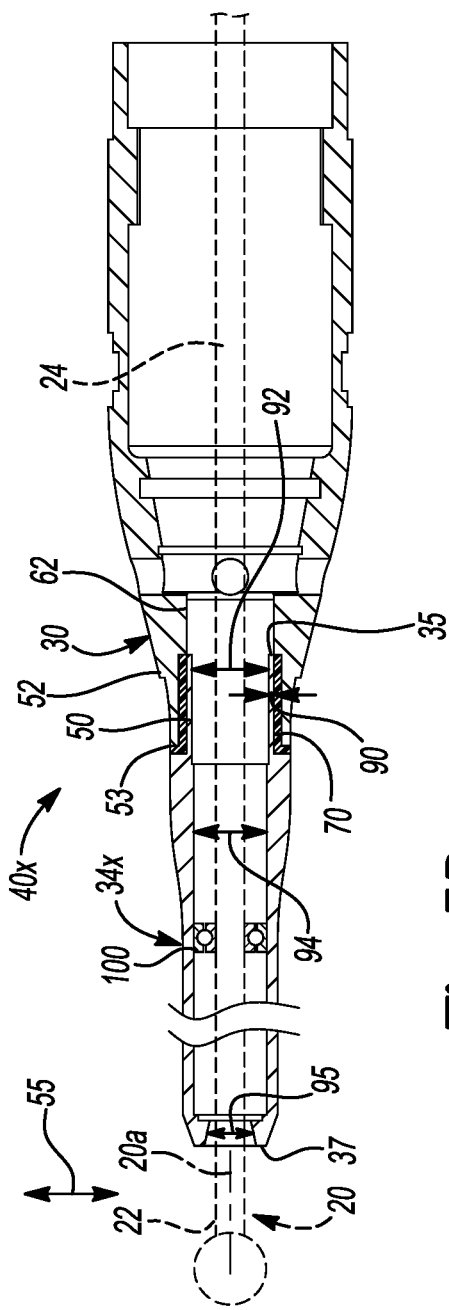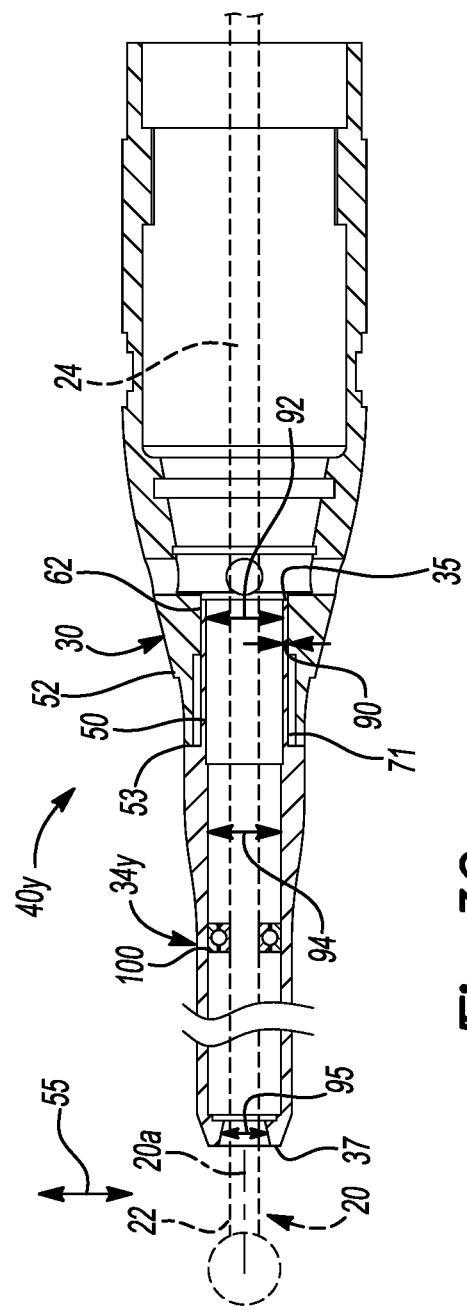

METHOD AND APPARATUS TO SELECT VIBRATION

CROSS-REFERENCE TO RELATED APPLICATIONS

The application is a continuation of U.S. patent application Ser. No. 16/276,090 filed on Feb. 14, 2019, which is a continuation of U.S. patent application Ser. No. 14/926,787 filed on Oct. 29, 2015, now U.S. Pat. No. 10,206,691 issued on Feb. 19, 2019. The entire disclosures of the above applications are incorporated herein by reference.

FIELD

The subject disclosure relates to reduce an amount of vibration, and particularly to lessening and minimizing vibrations of a handle due to movements of a tool bit.

BACKGROUND

This section provides background information related to the present disclosure which is not necessarily prior art.

A procedure may be performed on the subject to assist in removing selected material. In various procedures, such as a surgical procedure, tissues can be removed from a subject, such as excising or resecting tissue. Various tissues can include soft tissues or hard tissues. During removal or extension of a hard tissue, a motorized instrument may be used in the resection and incision of the tissue. During various procedures, such as procedures on a vertebra, the instrument may be used to remove boney tissue from near sensitive areas.

For example, during a spinal procedure, it may be selected to remove boney tissue from near nerves extending from the spinal column of the patient. The resection of bone tissue may be to assist in relieving pressure on nerves to alleviate pain. Resection, therefore, may be near sensitive tissue such as nerve bundles, where precise and controlled resection is selected.

SUMMARY

This section provides a general summary of the disclosure, and is not a comprehensive disclosure of its full scope or all of its features.

An assembly is disclosed that can couple to and hold a tool. The tool may be a resection tool, such as a bone resection tool. In various embodiments the tool can include an elongated shaft having a working end at the end of the shaft. The shaft may be coupled to a motor to provide torque to the tool to rotate the tool during an operation. The operation may include resecting bone tissue or other tissues from the subject.

The assembly includes an attachment assembly which holds the tool relative to the motor. The attachment assembly may include an attachment base and an attachment tube that can be coupled to a collet. The collet may include various gears and connection portions that transfer torque from the motor to the tool. The attachment may provide various features, such as a bore diameter, length, angle, and the like to allow selecting the tool to be operated by the motor. Further, the attachment assembly may include stiffness modification and/or damping features such as damping members, thicknesses, and the like to minimize and/or reduce vibration at a tool tip and caused by the tool felt and received by a user.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view of an instrument assembly according to various embodiments;

FIG. 1A is a perspective view of an angled attachment assembly;

FIG. 2 is a plan view of an attachment assembly, according to various embodiments;

FIG. 3A is a cross-sectional view of the attachment assembly of FIG. 2 taken along line 3A-3A;

FIG. 3B is a cross-sectional view of an alternative attachment assembly of FIG. 2 taken along line 3A-3A;

FIG. 3C is a cross-sectional view of an alternative attachment assembly of FIG. 2 taken along line 3A-3A;

DETAILED DESCRIPTION

Figure 4:
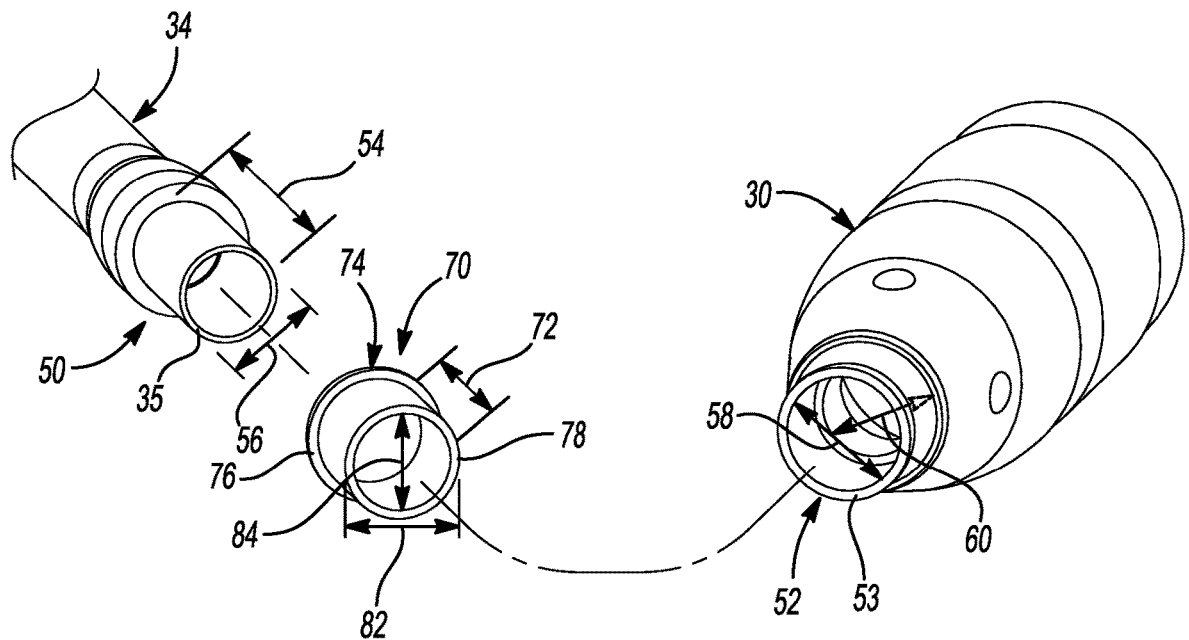
FIG. 4 is an exploded view of the attachment assembly of FIG. 3.

Example embodiments will now be described more fully with reference to the accompanying drawings.

With initial reference to FIGS. 1 and 2, an instrument assembly 10 is illustrated. The instrument assembly 10 can be similar to an instrument assembly used to resect tissue, for example the Straightshot® M4 Microdebrider powered handpiece or the Midas Rex® Legend EHS Stylusø High-Speed Surgical Drill, which may be selectively used for ear-nose-throat (ENT) or neurosurgery, sold by Medtronic, Inc. The instrument assembly 10 can include a motor housing 16 that extends along a long axis, and may have various angled or ergonomically shaped portions. The housing 16 may house a motor 17 and have a collet assembly 18. The collet 18 can house various portions, such as gears and connections to a motor within the motor housing 16 with a tool bit 20. The tool bit 20 can include a working end 22 and a shaft 24. The working end 22 can include a burr, drill bit, resection burr, or other appropriate working end. Nevertheless, the motor 17 can transfer torque to the working end 22 through the shaft 24 via an interconnection within the collet 18.

The instrument assembly 10 can further include an attachment base 30, also referred to as an attachment housing, and an attachment tube 34. The attachment tube 34 can be interconnected with the attachment base 30, as discussed further herein. The attachment tube 34 may form a bore 42 and both the attachment tube 34 and the bore 42 may extend from a first terminal end 35 to a second terminal end 37.

The attachment base 30 and the attachment tube 34 may be operably removed from the collet 18 during a selected procedure. For example, the attachment base 30 and the attachment tube 34 may form an attachment assembly 40 that can include various features, such as a selected size of a bore 42 that may extend through at least a portion of the attachment tube 34 and a geometry of the attachment tube 34. For example, the attachment tube 34 may be provided as an attachment tube 34', as illustrated in FIG. 1A, where the attachment tube 34 includes a first tube portion 34a extending along a first axis A and a second tube portion 34b that extends along a second axis B, where the axes A and B are angled relative to one another. The angle between the axis A and axis B can be selected based upon a selected procedure and may further include movable interconnections to provide power to the tool 20 from the motor 16 through the angled region. An angle may also be formed by connecting the attachment tube 34 to an attachment base that has an angle. For example, gears and connections may be provided within the attachment base between a proximal end and the connection end 50. Thus, an angle may be provided between the working end 22 of the tool 20 and the collet 18 without having the angled tube 34'. Nevertheless, the attachment assembly 40 may be removed from the collet assembly 18 to selectively choose an attachment that may include different features such as the length of the attachment tube 34, angle of the attachment tube, including the angle of the attachment tube 34', angle of the attachment base 30, and other features.

The attachment assembly 40 can include an interconnection of the attachment tube 34 with the attachment housing 30. As illustrated in FIG. 3A, the attachment tube 34 may be formed as a separate member from the attachment housing 30. The attachment tube 34 may then be selectively coupled to the attachment housing 30 using various connection mechanisms.

With continuing reference to FIG. 3A and additional reference to FIGS. 3B, 3C, and 4, the attachment assembly 40 will be discussed in greater detail. The attachment assembly 40 includes the attachment tube 34 that is engaged within the attachment base 30. The attachment tube 34 may generally include a cylindrical exterior. Further, the inner bore 42 may be formed by an internal annular wall. As discussed herein, various features may be formed into the annular wall to vary a diameter of the bore 42 at selected regions.

The attachment tube 34 may include a connection region 50 that is received within an attachment base receiving section 52. The connection region 50 may be formed at or near the first terminal end 37. In various embodiments, the connection region 50 may be formed at the first terminal end 35 and extend towards the second terminal end 37. The tube connection region 50 can extend a length 54 and include an outer diameter 56. The attachment portion 50 can be received within the receiving section 52 for coupling of the attachment tube 34 to the attachment base 30.

As discussed herein, the tube connection region 50 may have an external thread to engage an internal thread in the receiving section 52. It is understood, however, that other coupling mechanisms may be provided, such as at least one of a press-fit, a brazing, a welding, a threaded connection, an adhesive, a stake, or other appropriate connections may be used to connect the attachment tube 34 to the attachment base 30. Further, the attachment tube 34, in various embodiments, may be coupled both directly and indirectly to the attachment base 30 (illustrated in FIG. 3A), may be only indirectly coupled to the attachment base 30 (illustrated in FIG. 3B), or may be only coupled directly to the attachment base 30 (illustrated in FIG. 3C), as discussed herein.

The attachment section 52 of the attachment base 30 can include a first inner diameter 58 that may be greater than the outer diameter 56 to receive an intermediate or damping member 70 (also illustrated in FIG. 4). The receiving section 52 may further include a second inner diameter 60 that may be substantially equivalent to or slightly larger than the outer diameter 56 of the tube connection section 50. The relationship of the inner diameter 58 and the outer diameter 56 of the damping member 70 may allow or form a press-fit connection between the damping member 70 and the attachment base 30. When assembled, therefore, the connection region 50 of the attachment tube 34 may be generally concentric with the attachment region 52 of the attachment base 30.

The tool 20 may rotate around an axis 20a. The rotation may be caused by torque being transmitted to the tool 20 from the motor 17 within the motor assembly 16. Chatter may be caused by movement of the tool 20 and/or the instrument assembly 10 that is normal to the axis 20a, such as in the direction of the double-head arrow 55. It is understood, however, that rotation of the tool 20 may cause vibration in any lateral direction relative to the axis 20a. Operating the tool 20 at a selected rotational speed may also reduce vibrations, such as lateral movements away from the axis 20a by the tool 20 and/or the attachments assembly 40.

As illustrated in FIG. 3A, the connection region 50 of the attachment tube 34 may extend to a direct bonding region 62 to allow for direct connection of the attachment tube 34 to the attachment base 30. For example, in the direct bonding region 62, an external thread on the tube connection section 50 can engage inner threads that are formed on the inner diameter 60 of the connection region 52 at the direct bonding region 62. The attachment tube 34 may then be threaded to the attachment base 30 to allow for direct connection of the attachment tube 34 to the attachment base 30. It is understood, however, that other connections and bonding of the attachment tube 34 to the base 30 can be made. For example, selected adhesive materials, press fit, and other connections can be formed between the attachment tube 34 and the attachment base 30.

With reference to FIG. 3B, it is understood, that the attachment tube 34 need not be directly connected to the attachment base 30. Rather, an attachment assembly 40x may have an attachment tube 34x. The attachment tube 34x may be substantially similar to the attachment tube 34, discussed above. The attachment tube may have the connection portion 50 that may only contact the damping member 70 within the attachment base 30. Thus, the attachment tube 34 may be interconnected with the attachment base 30 via the damping member 70 and not have a direct contact to the attachment base 30, at least within the connection region 52. The attachment tube 34 may, however, contact an external surface 53 of the attachment base 30.

As illustrated in FIG. 3C, the attachment tube 34 need only directly contact and connect to the attachment base 30. Connecting the attachment tube only directly to the attachment base 34 may be a selected alternative to including the damping member 70. An attachment assembly 40y may have an attachment tube 34y. The attachment tube 34y may be substantially similar to the attachment tube 34, discussed above. The attachment tube 34y may have the connection portion 50 that may only contact the attachment base 30, including at the exterior surface 53 and the direct bonding region 62. Thus, a gap 71 may be formed if the internal diameter 58 is maintained. It is understood, however, that the connection region 52 may include only the internal diameter 60 such that no gap 71 is present.

With continuing reference to FIGS. 1-3C and additional reference to FIG. 4, the damping member 70 may extend a length 72 between an outer or distal end 74 that may include a lip or edge 76 and a proximal end 78. The damping member 70 may be generally cylindrical and have a substantially annular wall that forms an external diameter 82 and an internal diameter 84. The external diameter 82 may be substantially equivalent to or slightly smaller than the inner diameter 58 of the base connection region 52. Therefore, the damping member 70 may be press fit and held in the connection region 52. It is further understood, however, that the damping member 70 may be bonded to the attachment base 30 with an adhesive, a threaded connection, or other appropriate connection. The inner diameter 84 may be formed to receive the connection region 50 and may be substantially equivalent to or equal to the inner diameter 60 of the connection region 52.

It is further understood that the damping member 70, according to various embodiments, may be molded or formed onto the attachment base 30, the attachment tube 34, or both. For example, the damping member 70 may be injection molded into the connection 50 of the attachment tube 34 or the connection 52 of the attachment base 30. Thus, the connection of the damping member 70 may be made relative to the attachment assembly 40 in selected manners.

The damping member 70 may further have a thickness (formed by the difference between the internal diameter 84 and the outer diameter 82), length 72, material, or other features selected based upon operation parameters of the attachment assembly 40. The operational parameters may include a rotational speed of the tool 20, the length of the attachment tube 34, the angle of the attachment tube 34', the diameter of the shaft 24, etc. Still further, the damping member 70 may be selected of a material with a relatively high loss factor (i.e. ability to absorb and/or transform kinetic energy to another form of energy), but also suitable for a selected procedure. For example, a viscoelastic polymer may provide a selected loss factor while being able to withstand repeated heat and steam sterilization and/or chemical sterilization for an operative procedure on a human patient. The damping member 70 may, for example, be formed of an elastomer, a silicone rubber, FKM (as determined by ASTM D1418) or similar fluoroelastomer, chlorobutyl elastomer, or other polymer or elastomer material. One example includes Viton® fluoropolymer elastomer sold by E.I. du Pont de Nemours and Company or The Chemours Company having a place of business at Wilmington, Del.

As discussed above, in various embodiments, the tube connection region 50 can therefore be fitted within the inner diameter 84 of the damping member 70 and placed within the connection region 52 of the attachment base 30. According to various embodiments, as discussed above, the tube connection region 50 may extend no longer than the length 72 of the damping member 70. It is understood, however, that the attachment tube 34 may connect directly and only to the attachment base 30.

The damping member 70 may include the various characteristics discussed above to tune the vibration of the instrument assembly 70, such as at a portion held by a user at the base (30) or motor housing (16), and chatter at the tool tip 22. The damping member 70 may be tuned to dampen vibration and/or chatter a selected amount by selecting the thickness, length, material, location, etc. The reduced vibration and chatter may ensure a precise resection or operation of the assembly 10.

Tuning the vibration may occur without or in addition to the damping member 70 and characteristics of the damping member 70. For example, the attachment region 50 of the attachment tube 34 may include a selected wall thickness 90 to assist in reduction of vibration during operation of the tool 20. As illustrated in FIGS. 3A, 3B, and 3C, the tube connection region 50 can include the wall thickness 90 that can be selected according to various features and limitations of the system. The thickness 90 of the connection region 50 may be formed by increasing an internal diameter of the connection tube 34 on the selected portion of its length. For example, as illustrated in FIGS. 3A, 3B, and 3C, the thickness 90 is formed by an internal diameter 92 in a first portion of the attachment tube while an internal diameter 94 is formed in a second portion of the attachment tube 34. The attachment tube 34 may include other internal diameters, such as a terminal internal diameter 95 where the tool 20 extends from the attachment tube 34 near the working end 22 of the tool 20. It is understood, the attachment tube 34 may be coupled to the attachment base 30 without the damping member 70. The selected two internal diameters 92 and 94 forming the thickness may, therefore, alone provide a vibration reduction feature Reducing the vibration, therefore, may be created using one or more of the selected thickness, axial length of a region with a selected thickness, damping member, etc. Creating a selected vibration design limitation, including reducing vibrations with a selected feature, may be selected by reducing or forming a selected thickness at a selected location. The reduced or formed thickness may be by cutting or forming an internal diameter or cutting into an outer surface of the attachment tube 34.

As briefly discussed above, during operation, the tool 20 may rotate around the axis 20a in selected directions and may oscillate. During rotation and oscillation of the tool 20, vibrations may be induced in the attachment assembly 40. The vibrations may be due to rotation of the tool 20 or operation of a motor in the motor housing or motor assembly 16. The vibrations may be reduced by either or both (i.e. combined) the thickness 90 of the attachment tube 34 and the damping member 70. As noted above, the reduction in vibration and chatter may be achieved by forming the selected thickness 90 at any appropriate axial positional along the attachment tube 34. The tool shaft 24 may ride in one or more bearings 100 that are connected within the internal diameter 94 of the attachment tube 34. Therefore, rotation of the tool 20 may be radially guided by the attachment tube 34. This may transmit vibrations to the attachment housing 30, the attachment tube 34, and may be transmitted to motor 16 or other portion grasped by a user.

Figure 5:
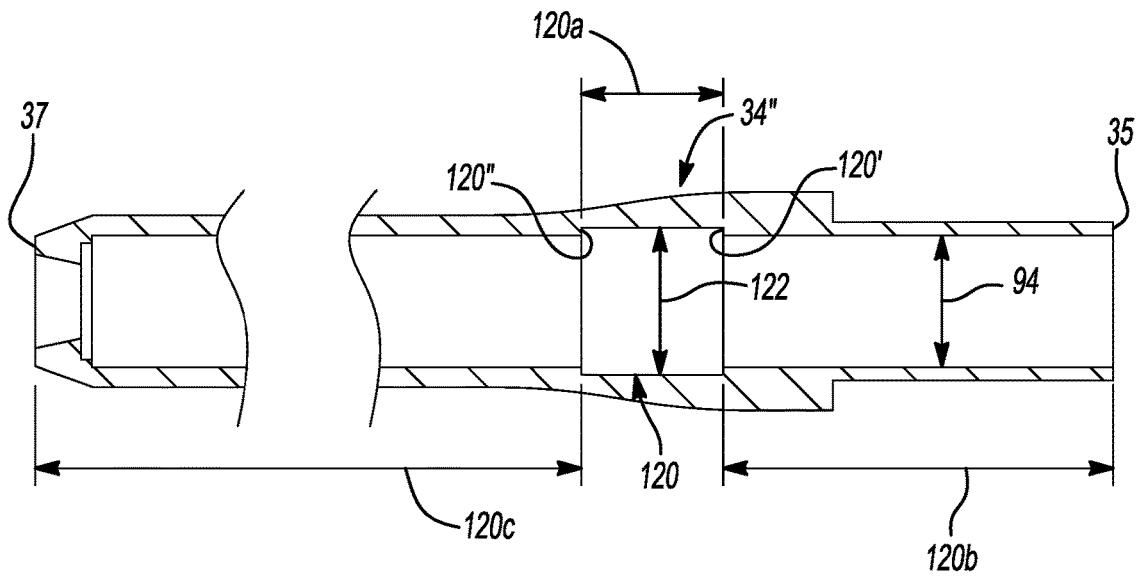
FIG. 5 is a cross-sectional view of an attachment tube along a longitudinal axis of the attachment tube, according to various embodiments.

The attachment tube 34, therefore, includes the selected thickness 90 and may be tuned relative to an operation of the tool 20 and geometries and configurations of the attachment tube 34 and/or the attachment base 30. For example, the internal diameter 94 of the bore 33 extending through the attachment tube, the length of the attachment tube 34, a geometry of the attachment base 30, a geometry of the attachment tube 34, such as the angle attachment tube 34', may all be considered when determining the selected thickness 90 of the attachment tube 34. Furthermore, a size, including a thickness, such as the difference between the internal diameter 84 and the external diameter 82 of the damping member 70, may be selected for tuning vibrational reduction of the attachment assembly 40 and/or the tool assembly 10. Tuning of vibration felt by a user, such as a surgeon, and tuning of chatter (i.e. lateral movement of the tool head 22) may be based on various features, as discussed herein. Further, specifics of the features, including size, placement, etc. may be based on specifics of the selected attachment assembly. As discussed above, various attachment assemblies may be provided in various configurations such that the specifics of the tuning features may vary amongst the attachment assemblies. Thus, one will understand that tuning of, such as selecting an amount of eliminating vibration and chatter, may vary based on upon several considerations. Moreover, it is understood that an attachment tube 34", as illustrated in FIG. 5, may include a selected thickness as a vibration reduction or tuning feature away from the terminal ends, including the first terminal end 35. For example, the attachment tube 34" may include the internal diameter substantially along an entire length of the attachment tube 34". However, a vibration reducing or tuning feature 120 may be formed as a notch or a groove within or external to the attachment tube 34 to form at least a region having an internal diameter 122. The internal diameter 122 provides a selected thickness relative to an external diameter of the attachment tube 34". The vibration reduction feature 120 may include a complete annular groove or may include formed struts or connections therein.

Moreover, the vibration reduction feature 120 may provide a selected flexibility at a selected position along a length of the attachment tube 34" to assist in mitigating or eliminating a selected vibration during the operation of the tool tip 20. For example, the vibration reduction feature may have a length 120a. The vibration reduction feature 120 may have a first end 120' spaced a distance 120b from the terminal end 35 and a second end 120" spaced a distance 120c from the second terminal end 120c. The selected lengths of 120a, 120b, and 120c can assist in tuning the dampening feature and may be selected based upon characteristics of the tube 34" and or the tool 20 and or the attachment base 30. Further, the relationship of the internal diameters 122 and 94 may be further selected to tune the dampening amount. The internal diameters 122 and 94 and sections having them may also be selectively placed along the length of the attachment tubes 34, 34', and 34".

As discussed above, the bearing 100 may be positioned within the attachment tube 34" and operation of the tool 20 rotating around the axis 20a may cause vibration in the attachment assembly 40. The vibration reduction feature 120 including the internal diameter 122 relative to the internal diameter 94 of the attachment tube 34" can provide a selected reduction of the vibration. The attachment tube 34" can be connected with the attachment base 30 in a manner substantially similar to that illustrated in FIG. 3A 3B or 3C, either directly to the attachment base 30, interconnection through the damping member 70 only, or a combination of interconnection to both a damping member 70 and direct attachments to the attachment base 30.

Accordingly, it is understood that the attachment tube 34 can be formed to include a vibration reduction or tuning feature such as the feature 120, illustrated in FIG. 5, or a thickness 90 of a wall as illustrated in FIG. 3A, 3B, or 3C, either alone or in combination with a damping member 70. The vibration reduction features can assist in tuning vibration, which may include minimizing or eliminating vibration, due to operation of the instrument assembly 10 to rotate the tool 20 around the axis 20a. By reducing the vibration, unselected movements of the instrument may be reduced and operation of the tool 20 may be smoother. This can allow for substantially precise operation of the tool 20, especially over long periods of time, to allow for speed of an operation and selected outcomes for a patient. Reducing vibration may also reduce user fatigue.

Figure 6:
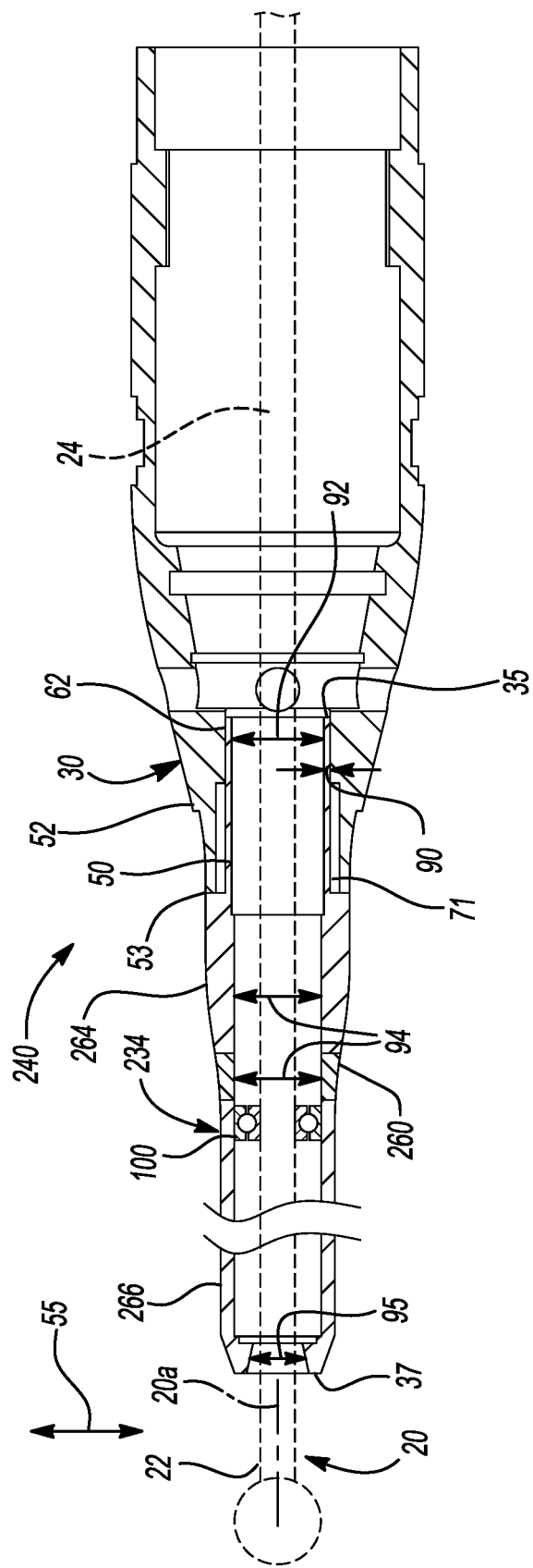
FIG. 6 is a cross-sectional view of an attachment assembly, according to various embodiments. Corresponding reference numerals indicate corresponding parts throughout the several views of the drawings.

With reference to FIG. 6 an attachment assembly 240 is illustrated. The attachment assembly 240 is similar to the attachment assembly 40, as discussed above. The attachment assembly 240, illustrated in cross-section FIG. 6, is understood to include the bore which may include the internal diameter 92 and the second and different internal diameter 94. Further, the attachment assembly 240 may include the attachment base 30, as discussed above, and an attachment tube 234 connected to the attachment base 30 in at least one of various manners. The attachment tube 234 may be (1) only connected directly to the attachment base 30, (2) interconnected with a damping member (not illustrated in FIG. 6) which is connected to the attachment base 30, or (3) connected to both a damping member and the attachment base 30 (not specifically illustrated in FIG. 6) according to various embodiments including features of those embodiments discussed above. The attachment assembly 240 can further include the connection portion 52 of the attachment base 30 and the connection portion 50 of the attachment tube 234.

The attachment tube 234 may include various interconnected portions, such as a damping member 260 that interconnects a first rigid member 264 and a second rigid member 266. The rigid members 264, 266 can include selected exterior dimensions, including those discussed above, and further include the internal diameters 92 and/or 94. Further, the damping member 260 can also define the internal diameter 94. It is understood, however, that the damping member 260 can have a selected axial position on the attachment tube 234, mass, length, density, internal diameter, or the like, as discussed above. Further, the damping member 260 can be formed of various materials, including those discussed above.

The attachment tube 234 may be connected to the attachment base 30, as discussed above. However, the damping member 260 may be included as a feature of the attachment tube 234 or between a portion of the attachment tube 234 and the attachment base 30. As illustrated in FIG. 6, the attachment base 30 can connect with the first rigid portion 264 and the damping member 260 can be positioned between a portion of the attachment tube 234, including the second rigid portion 266, and the attachment base 30. Therefore the damping member 260 is positioned between at least a portion of the attachment tube 234 (i.e., the second rigid member 266) and the attachment base 30. In various configurations, one skilled in the art may consider the first rigid portion 264, when connected with the attachment base 30, a portion of the attachment base 30. However, it is understood, that another damping member, such as the damping member 70, may be positioned generally near the connection and areas 50, 52 such as in the gap 71. Therefore, it is further understood, that the attachment assembly 240, according to various embodiments, may include a plurality of damping members. As specifically illustrated in FIG. 6, the damping member 260 is positioned a distance from the distal end 53 of the attachment base 30 and is completely integrated into the attachment tube 234.

The damping member 260 may be connected to the rigid members 264, 266 according to various appropriate bonding techniques. For example, the damping member 260 may be adhered, welded, directly molded onto the rigid members 264, 266, or other appropriate bonding or fixation techniques. Nevertheless, the damping member 260 may dampen motion between the second rigid member 266 and the first rigid member 264 and the attachment base 30. Therefore, the damping member 260, including various features of the damping member 260, may be used to assist in tuning chatter and vibration of an instrument 10, as discussed above.

The vibration reduction features can be tuned individually or collectively to specific configurations of the tool assembly 10, as noted above. For example, configurations of the tool assembly may include the size of the bore, length of the attachment tube 34, angle of the attachment tube 34', etc. The tuning feature(s) may include selecting a thickness of the thickness 90 of the wall, a length of the region having the thickness 90, an axial position of the wall with the thickness 90, thickness and/or length or axial positioning of the damping member 70, and/or axial position, length, or relative internal diameter of the dampening feature 120.

Vibration responses and associated reductions (e.g. by damping or increases in stiffening or decreases in stiffening) of the tool 20 and attachment assembly 40 can be modeled by one or more Structural Dynamic techniques. The modeling techniques may include modal analysis, harmonic analysis, or transient dynamic analysis. Also, or alternatively, various physical testing techniques may be used to determine the vibration responses. These methods may predict the frequencies and displacements involved as appropriate to the technique.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An assembly for holding a tool, comprising:
an attachment base configured to be operably coupled to a motor housing assembly;
an attachment tube extending from a first terminal end to a second terminal end; and
a damping member positioned between the attachment base and at least a portion of the attachment tube,
wherein the attachment tube is coupled to the attachment base at the first terminal end,
wherein the second terminal end of the attachment tube extends from the attachment base, and wherein the attachment base includes:
an attachment base receiving section and the attachment tube includes a connection region at the first terminal end that is received within the attachment base receiving section, the connection region including a first inner diameter extending along the attachment base receiving section and a second inner diameter extending from an end of the attachment base receiving section, the first inner diameter being larger than the second inner diameter.

2. The assembly of claim 1, wherein the attachment tube extends within and directly contacts only the damping member positioned within the attachment base.

3. The assembly of claim 2, wherein the damping member directly contacts the attachment base.

4. The assembly of claim 1, wherein the attachment tube includes a connection region at the first terminal end that directly contacts the damping member and the attachment base.

5. The assembly of claim 4, wherein the connection region of the attachment tube has a first length and the damping member has a second length, the first length being longer than the second length.

6. The assembly of claim 1, wherein the motor housing includes:
an attachment connection; and
a motor housed within the motor housing.

7. The assembly of claim 1, wherein the damping member is formed of an elastomer material, a silicone rubber, a FKM (as determined by ASTM D1418), a fluoroelastomer, or a chlorobutyl elastomer.

8. The assembly of claim 1, wherein the attachment tube is directly connected to the attachment base at a first portion of a tube attachment section and directly contacts the damping member at a second portion of the tube attachment section between the attachment tube and the attachment base.

9. The assembly of claim 1, wherein the tool extends through the attachment base and the attachment tube.

10. The assembly of claim 1, wherein the attachment base has an internal wall surface and the attachment tube includes an external wall surface configured to fix the attachment tube to the attachment base with at least one of a press-fit, a brazing, a welding, a threaded connection, an adhesive, or a stake.

11. The assembly of claim 1, wherein the damping member is positioned within a tube connection bore in the attachment base to surround at least a portion of the attachment tube near the first terminal end, wherein the damping member is positioned between the attachment base and the attachment tube.

12. The assembly of claim 11, wherein the damping member is an annular member that extends from a first end to a second end and includes a radially extending flange at the first end.

13. An assembly for holding a tool, comprising:
an attachment base having a motor housing connection configured to be operably coupled to a motor housing;
an attachment tube extending from a first terminal end to a second terminal end, the attachment tube having a first vibration reduction feature formed by at least a selected thickness of a wall of the attachment tube positioned between the first terminal end and a second terminal end; and
a damping member positioned between the attachment base and the attachment tube,
wherein the attachment tube is coupled to the attachment base at an attachment base connection near the first terminal end,
wherein the second terminal end of the attachment tube extends from the attachment base, and
wherein the damping member provides a second vibration reduction feature.

14. The assembly of claim 13, wherein the damping member is an annular member that extends from a first end to a second end and includes a radially extending flange at the first end.

15. The assembly of claim 13, wherein the damping member is formed of an elastomer material, a silicone rubber, a FKM (as determined by ASTM D1418), a fluoroelastomer, or a chlorobutyl elastomer.

16. The assembly of claim 13,
wherein
the motor housing includes a motor configured to drive a tool.

17. The assembly of claim 13, wherein the damping member is positioned between an outer wall of the attachment tube and an inner wall of the attachment base.

18. The assembly of claim 13, wherein the first vibration reduction feature includes a first inner diameter of the attachment tube at the first terminal end and a second inner diameter a distance away from the first terminal end, wherein the first diameter is larger than the second diameter.

19. An assembly for holding a tool, comprising:
an attachment base configured to be operably coupled to a motor housing assembly;
an attachment tube extending from a first terminal end to a second terminal end; and
a damping member positioned between the attachment base and at least a portion of the attachment tube,
wherein the attachment tube is coupled to the attachment base at the first terminal end,
wherein the second terminal end of the attachment tube extends from the attachment base, and
wherein the attachment tube extends within and directly contacts only the damping member positioned within the attachment base.

20. The assembly of claim 19, wherein the damping member directly contacts the attachment base.

21. An assembly for holding a tool, comprising:
an attachment base configured to be operably coupled to a motor housing assembly;
an attachment tube extending from a first terminal end to a second terminal end; and
a damping member positioned between the attachment base and at least a portion of the attachment tube,
wherein the attachment tube is coupled to the attachment base at the first terminal end,
wherein the second terminal end of the attachment tube extends from the attachment base,
wherein the attachment tube includes a damping member disposed between the first terminal end and the second terminal end,
wherein the attachment tube defines a first inner diameter extending from the first terminal end to the damping member,
wherein the attachment tube defines a second inner diameter extending proximal from the damping member to the second terminal end, and
wherein the first inner diameter is greater than the second inner diameter.

22. An assembly for holding a tool, comprising:
an attachment base configured to be operably coupled to a motor housing assembly;
an attachment tube extending from a first terminal end to a second terminal end; and
a damping member positioned between the attachment base and at least a portion of the attachment tube,
wherein the attachment tube is coupled to the attachment base at the first terminal end,
wherein the second terminal end of the attachment tube extends from the attachment base,
wherein the damping member is positioned within a tube connection bore in the attachment base to surround at least a portion of the attachment tube near the first terminal end,
wherein the damping member is positioned between the attachment base and the attachment tube, and
wherein the damping member is an annular member that extends from a first end to a second end and includes a radially extending flange at the first end.

* * * * *